United States Patent [19]

Walsh

[11] 4,440,785
[45] Apr. 3, 1984

[54] METHODS OF USING 2-AMINOBIPHENYLACETIC ACIDS, ESTERS, AND METAL SALTS THEREOF TO TREAT INFLAMMATION

[75] Inventor: David A. Walsh, Richmond, Va.

[73] Assignee: A. H. Robins Company, Inc., Richmond, Va.

[21] Appl. No.: 339,211

[22] Filed: Jan. 13, 1982

Related U.S. Application Data

[60] Continuation-in-part of Ser. No. 202,287, Oct. 30, 1980, abandoned, which is a division of Ser. No. 64,767, Aug. 8, 1979, abandoned, which is a continuation-in-part of Ser. No. 851,641, Nov. 15, 1977, abandoned.

[51] Int. Cl.³ .................... A61K 31/19; C07C 149/43
[52] U.S. Cl. ........................................ 424/317; 560/16; 548/486; 562/433; 562/457
[58] Field of Search ........................... 560/16; 424/317

[56] References Cited

U.S. PATENT DOCUMENTS

| | | | |
|---|---|---|---|
| 3,466,372 | 9/1969 | Shen et al. | 424/250 |
| 3,784,704 | 1/1974 | Cohen et al. | 424/317 |
| 3,894,080 | 7/1975 | Diamond et al. | 560/16 |
| 3,966,978 | 6/1976 | Ellenbogen et al. | 424/317 |
| 4,048,332 | 9/1977 | Adams et al. | 424/272 |

FOREIGN PATENT DOCUMENTS 831029  12/1969  Canada ................................. 560/16

*Primary Examiner*—Donald G. Daus
*Assistant Examiner*—S. A. Gibson

[57] ABSTRACT

Novel 2-aminobiphenylacetic acids, esters and metal salts of the formula are disclosed:

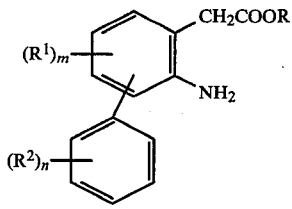

wherein R represents hydrogen, lower alkyl, sodium or potassium; $R^1$ represents fluoro, chloro, bromo, lower-alkyl or amino; $R^2$ represents lower-alkyl, lower-alkoxy, fluoro, chloro, bromo, amino or trifluoromethyl; and m and n are 0–2 with the proviso that when $R^1$ or $R^2$ are tertiary butyl or a sterically hindering lower alkyl radical, m and/or n are 1. The compounds are prepared by hydrolysis of 4-(5-, 6- and 7-)phenylindolin-2-ones to give the 2-amino-3-(4-, 5- and 6-)biphenylacetic acids. The free acids are converted to the esters and metal salts. The compounds have anti-inflammatory activity and inhibit blood platelet aggregation.

8 Claims, No Drawings

METHODS OF USING 2-AMINOBIPHENYLACETIC ACIDS, ESTERS, AND METAL SALTS THEREOF TO TREAT INFLAMMATION

REFERENCE TO PARENT PATENT APPLICATION

This application is a continuation-in-part of U.S. patent application Ser. No. 06/202,287 filed Oct. 30, 1980 now abandoned, which is a division of U.S. patent application Ser. No. 064,767, filed Aug. 8, 1979, now abandoned, which is a continuation-in-part of U.S. patent application Ser. No. 851,641, filed Nov. 15, 1977, now abandoned.

BACKGROUND OF THE INVENTION

The present invention relates to novel biphenylacetic acids, esters and metals salts and is more particularly concerned with certain 2-amino-biphenylacetic acids, compositions thereof, methods for the production thereof and use of the same.

Various biphenylacetic acids have been demonstrated to possess anti-inflammatory activity as disclosed in U.S. Pat. Nos. 3,784,704 and 3,966,978. Biphenylacetic acids and esters having an amino substituent in the phenyl ring attached to the phenyl ring having the acetic acid moiety are disclosed in French Patent M 5,737 [(CA 70, 114837d (1969)]. German Offenlegungsschrift 2,355,084 discloses methyl 3-amino-4-biphenylacetate as an intermediate in the preparation of phenanthridones.

OBJECTS AND SUMMARY OF THE INVENTION

It is an object of the present invention to provide novel 2-aminobiphenylacetic acids, esters, and metal salts and to provide methods for the preparation of such novel compounds.

It is another object of the present invention to provide a method for using the novel compounds of the present invention for treatment of a living animal body, especially mammalian bodies, to inhibit blood platelet aggregation and provide anti-inflammatory activity.

It is yet another object of the present invention to provide novel compositions comprising the novel compounds of the present invention.

In one aspect of the present invention there is provided a compound having the formula:

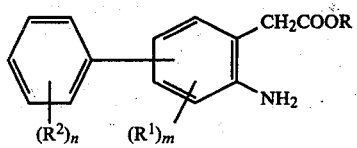

wherein:
R is a hydrogen, lower alkyl, sodium or potassium,
$R^1$ is fluoro, chloro, bromo, lower alkyl or amino,
$R^2$ is lower alkyl, lower alkoxy, fluoro, chloro, bromo, amino or trifluoromethyl,
m and n are 0–2 with the proviso that when $R^1$ or $R^2$ are tertiary butyl or a sterically hindering lower alkyl radical, m and/or n are 1; and wherein the phenyl substituent is in the 3, 4 or 5 position.

In another aspect of the present invention there is provided a compound having the formula:

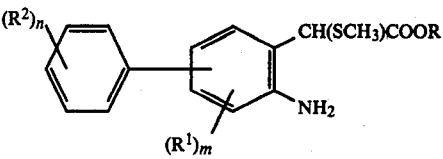

wherein:
R is lower alkyl,
$R^1$ is fluoro, chloro, bromo, lower alkyl or nitro,
$R^2$ is lower alkyl, lower alkoxy, fluoro, chloro, bromo, nitro or trifluoromethyl, and
m and n are as defined above.

In another aspect of the present invention there is provided a compound having the formula

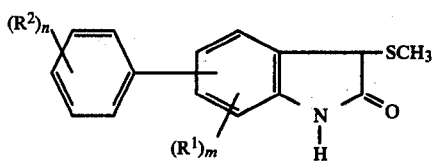

wherein:
$R^1$ is fluoro, chloro, bromo, lower alkyl or nitro,
$R^2$ is lower alkyl, lower alkoxy, fluoro, chloro, bromo, nitro or trifluoromethyl, and
m and n are as defined above.

In yet another aspect of the present invention there is provided a therapeutic composition suitable for alleviating inflammation comprising (a) an effective amount of a compound selected from the group having the formula as defined in Formula I above,
wherein:
R is hydrogen, lower alkyl, sodium or potassium,
$R^1$ is fluoro, chloro, bromo, lower alkyl or amino,
$R^2$ is lower alkyl, lower alkoxy, fluoro, chloro, bromo, amino or trifluoromethyl,
m and n are as defined above, and
wherein the phenyl substituent is in the 3, 4 or 5 position, and (b) a pharmaceutically acceptable carrier therefor.

In still yet another aspect of the present invention there is provided a method for alleviating inflammation in a living animal body with a minimum of undesirable side effects comprising internally administering to said living animal body an effective amount of a compound having the formula as defined in Formula I above, wherein:
R is hydrogen, lower alkyl, sodium or potassium,
$R^1$ is fluoro, chloro, bromo, lower alkyl or amino,
$R^2$ is lower alkyl, lower alkoxy, fluoro, chloro, bromo, amino or trifluoromethyl,
m and n are as defined above, and
wherein the phenyl substituent is in the 3, 4 or 5 position.

In another aspect of the present invention there is provided a process for the preparation of a 4-(5-, 6-, or 7-) phenylindolin-2-one of the formula:

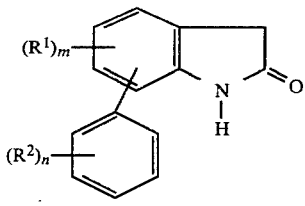

wherein:
R¹ is fluoro, chloro, bromo, lower alkyl or amino,
R² is lower alkyl, lower alkoxy, fluoro, chloro, bromo, amino or trifluoromethyl, and
m and n are as defined above which comprises the steps of
(1) reacting at −65° to −78° C. a biphenylamine of the formula

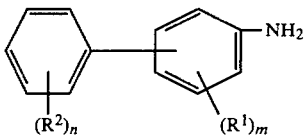

wherein R¹, R², m and n are defined above with t-butylhypochlorite and a lower alkyl-α-(methylthio) acetate of the formula

CH₂(SCH₃)COOR and then with triethylamine to give a lower alkyl 2-amino-3-(4, 5-, or 6-)phenyl-α-methylthiophenylacetate of the formula

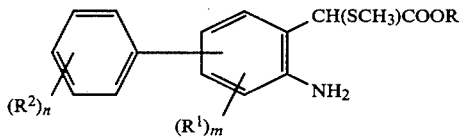

wherein R¹, R², m and n are as defined above and R is lower alkyl, (2) reacting the lower alkyl 2-amino-3-(4-, 5-, or 6-)phenyl-α-methylthiophenylacetate prepared in step (1) with a dilute mineral acid at 20° C. to 75° C. to give a 3-methylthio-4-(5-, 6-, or 7-)phenylindolin-2-one of the formula

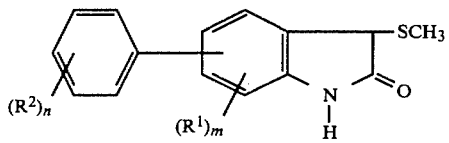

wherein R¹, R², m and n are as defined above; and (3) stirring the 3-methylthio-4-(5-, 6-, or 7-)phenylindolin-2-one prepared in step (2) with Raney nickel or tinhydrochloric acid in an inert atmosphere to remove the 3-methylthio radical to give the 4-(5-, 6-, or 7-)phenylindolin-2-one of the formula

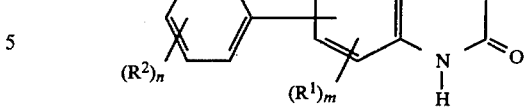

wherein R¹, R², m and n are as defined above.

In still another aspect of the present invention there is provided a process for the preparation of a 2-amino-3-(4-, 5-, or 6-)biphenylacetic acid of the formula as defined in Formula I above,
wherein:
R¹ is fluoro, chloro, bromo, lower alkyl or amino,
R² is lower alkyl, lower alkoxy, fluoro, chloro, bromo, amino or trifluoromethyl, and
m and n are as defined above,
which comprises hydrolyzing in aqueous basic solution a 4-(5-, 6- or 7-)phenylindolin-2-one of the formula

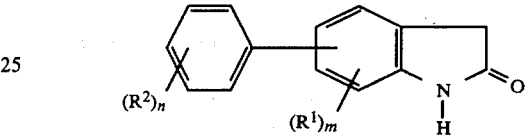

wherein R¹, R², m and n are as defined above and neutralizing the aqueous basic solution to form the free 2-amino-3-(4-, 5-, or 6-)biphenylacetic acid.

In another aspect of the present invention there is provided a therapeutic composition suitable for inhibiting blood platelet aggregation comprisig (a) an effective amount of a compound selected from the group having the formula as defined in Formula I above,
wherein:
R is hydrogen, lower alkyl, sodium, or potassium,
R¹ is fluoro, chloro, bromo, lower alkyl, or amino,
R² is lower alkyl, lower alkoxy, fluoro, chloro, bromo, amino, or trifluoromethyl,
m and n are as defined above, and
(b) a pharmaceutically acceptable carrier therefor.

In another aspect of the present invention there is provided a method of inhibiting blood platelet aggregation in a living animal body comprising internally administering to said living animal body an effective amount of a compound having the formula as defined in Formula I above wherein:
R is hydrogen, lower alkyl, sodium, or potassium.
R¹ is fluoro, chloro, bromo, lower alkyl, or amino,
R² is lower alkyl, lower alkoxy, fluoro, chloro, bromo, amino, or trifluoromethyl, and
m and n are as defined above.

DETAILED DESCRIPTION OF THE INVENTION

The novel compounds of this invention are useful as anti-inflammatory agents and inhibit blood platelet aggregation. The compounds may be administered alone or with suitable pharmaceutical carriers to warm blooded animals, mammals such as felines, canines and humans and can be in solid or liquid form as, for example, tablets, capsules, powders, solutions, suspensions or emulsions.

The compounds can be administered orally, parenterally, subcutaneously or intramuscularly. The unit dosage form can contain 1 to 50 milligrams of a novel compound of this invention and can be administered in a single does or in multiple doses up to about 450 milligrams.

The solid unit dosage form can be a gelatin capsule containing a novel compound of this invention and a pharmaceutically acceptable filler or carrier such as sucrose, lactose, corn starch and the like. Tablets containing the novel compounds represent another embodiment of this invention and are prepared using conventional tableting materials.

The novel concept of the present invention resides in the provision of therapeutically active biphenylacetic acids, the esters and alkali metal salts thereof which have a primary amino group ortho to the acetic acid group. Therapeutically active compounds possessing such an arrangement have been heretofore unknown prior to the present invention.

The anti-inflammatory utility of the novel compounds of this invention was determined using a modification of the Evans Blue-Carrageenan Pleural Effusion Assay of Sancilio, L. F., J. Pharmacol. Exp. Ther. 168, 199–204 (1969).

The novel compounds of the present invention also possess blood platelet aggregation activity. For example, a 2-amino-3-biphenylacetic acid hydrate provided 65 percent inhibition at a dosage of 100 mg/kg.

In the definition of symbols in the formulae hereof and where they appear elsewhere throughout this specification, the terms have the following significance.

The term "lower alkyl" as used herein includes straight and branched chain radicals of up to six carbon atoms inclusive, preferably no more than four carbon atoms, and is exemplified by such groups as methyl, ethyl, propyl, isopropyl, butyl, sec. butyl, tertiary butyl, amyl, isoamyl and hexyl. The term "lower alkoxy" has the formula —O—lower alkyl.

When $m=2$ or $n=2$, $R^1$ or $R^2$ can be the same or different radicals.

The preferred alkali metal salts of Formula I are the sodium and potassium salts. The salts are also useful intermediates for the preparation of the esters of Formula I.

The salts and the free acids can contain water of crystallization, therefore the salts and the free acids containing various degrees of hydration are included within the scope of the invention.

METHOD OF PREPARATION

The compounds of Formula I wherein R represents hydrogen may be prepared by hydrolysis of 4-(5-, 6-, and 7-)phenylindolin-2-ones (II) in aqueous basic solution followed by neutralization of the basic reaction mixture with a suitable organic acid such as acetic acid or a dilute mineral acid as indicated by the following:

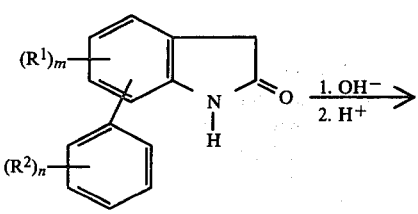

II

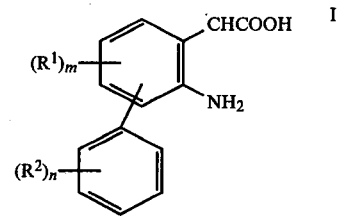

I wherein $R^1$, $R^2$, m and n are as defined hereinabove.

The hydrolysis of an indolin-2-one (II) is carried out in dilute aqueous base as, for example, 3 N sodium hydroxide solution, for a period of from about 1.0 to about 60 hours, usually until the indolin-2-one has dissolved. The hydrolysis may be run in an inert atmosphere using nitrogen. The hydrolysis mixture may be filtered to remove base-insoluble materials and the pH of the basic solution is adjusted to pH 6-pH 7 by the addition of a weak organic acid such as glacial acetic acid or a dilute mineral acid such as hydrochloric acid. When the sodium or potassium salt is to be prepared the desired salt separates from the cooled basic reaction mixture or it is isolated by concentration of the reaction mixture and the salt separates from the cooled concentrated solution.

The lower alkyl esters of Formula I are preferably prepared from the acids which are converted to an alkali metal salt, preferably the sodium or potassium salt which is isolated, dried and then reacted in a suitable solvent as, for example, dimethylformamide, with an alkyl halide, preferably an alkyl iodide, to furnish the desired ester.

The 4-(5-, 6- and 7-)phenylindolin-2-ones (II) are prepared from appropriately substituted biphenylamines (V) by the following reaction sequence, wherein $R^1$ and $R^2$ have the values hereinabove defined except additionally $R^1$ and $R^2$ may be nitro in Formulas III, IV and V, and R is lower alkyl, preferably ethyl. The reaction conditions employed are more fully set forth hereinafter in the specific preparations which follow.

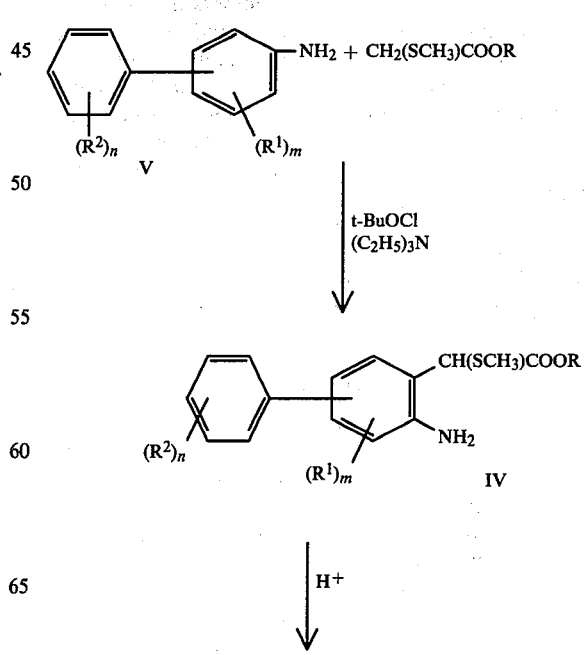

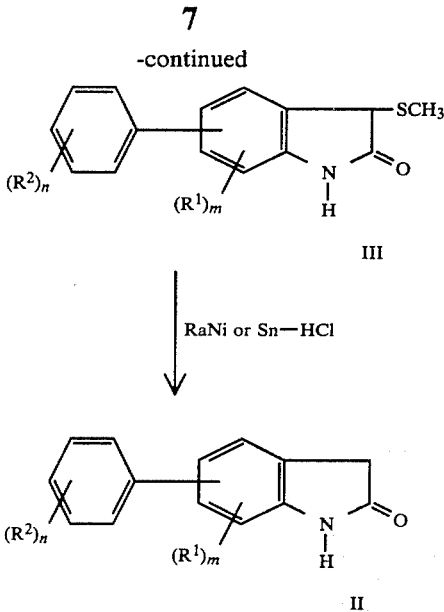

Compounds of Formula II wherein $R^1$ or $R^2$ is $NH_2$, are prepared from the corresponding biphenyl amine wherein $R^1$ or $R^2$ is $NO_2$, the resulting $NO_2$ radical in Formula III being reduced by RaNi or Sn/HCl at the same time as the methylthio group is removed. Additional reducing agent is required and in the instance of tin, three additional moles per mole of $NO_2$ are required as well as sufficient HCl to maintain acid conditions.

PREPARATION 1

3-Methylthio-5-phenylindolin-2-one

A solution of 21.4 g. (0.13 mole) of 4-aminobiphenyl in 400 ml. of methylene chloride was cooled to −65° C. and treated with 17.0 g. (0.13 mole) of ethyl 2-methylthioacetate and then 14.2 g. (0.132 mole) of t-butylhypochlorite while maintaining the temperature below −60° C. The reaction mixture was stirred at −65° C. for 1.5 hr., treated with 13.3 g. (0.132 mole) of triethyl amine and allowed to warm to ambient temperature. The solution was washed twice with water and concentrated. The residue was dissolved in 200 ml. of methanol, 40 ml. of 3 N hydrochloric acid was added, and the mixture was refluxed over night. The solution was concentrated until a solid began to precipitate. The mixture was cooled, and the solid was collected by filtration, recrystallized once from methanol and twice from benzene to yield 6.0 g. (18%) of product as a white solid, m.p. 170°-2° C.

Analysis: Calculated for $C_{15}H_{13}NOS$: C, 70.56; H, 5.13; N, 5.49; Found: C, 70.82; H, 5.13; N, 5.41.

PREPARATION 2

5-Phenylindolin-2-one

To a slurry of 11.2 g. (0.044 mole) of 3-methylthio-5-phenylindolin-2-one in 500 ml. of tetrahydrofuran was added 100 g. of a commercial Raney nickel/water preparation portionwise over a 2 hr. period. The mixture was filtered through celite and the filtrate was concentrated. A small amount of methylene chloride was added to the residue and the resulting solid was collected by filtration. This solid was recrystallized from toluene to give 6.2 g. (67%) of product as a tan solid, m.p. 214°-15° C.

Analysis: Calculated for $C_{14}H_{11}NO$: C, 80.36; H, 5.30; N, 6.69; Found: C, 80.00; H, 5.22; N, 6.60.

PREPARATION 3

3-Methylthio-7-phenylindolin-2-one

A solution of 25.5 g. (0.15 mole) of 2-aminobiphenyl in 450 ml. of methylene chloride was cooled to −65° C. and treated with 20.1 g. (0.15 mole) of ethyl 2-methylthioacetate. Immediately 16.7 g. (0.155 mole) of t-butylhypochlorite was added dropwise over a 15 min. period while the temperature was maintained at −65° C. The reaction mixture was stirred at −65° C. for 1.5 hr., 15.5 g. (0.155 mole) of triethylamine was added, and the mixture was allowed to warm to ambient temperature. The solution was washed with two 100 ml. portions of water and then concentrated. The residue was mixed with 200 ml. of methanol, the mixture heated to reflux, 40 ml. of 3 N hydrochloric acid was added and the mixture refluxed overnight. The solution was cooled and the resulting solid was collected by filtration, washed with methanol and recrystallized from benzene to yield 25.3 g. (66%) of product as tan needles, m.p. 164°-6° C.

Analysis: Calculated for $C_{15}H_{13}NOS$: C, 70.56; H, 5.13; N, 5.49; Found: C, 70.71; H, 5.23; N, 5.53.

PREPARATION 4

7-Phenylindolin-2-one

A stirred solution of 21.5 g. (0.084 mole) of 3-methylthio-7-phenylindolin-2-one in 400 ml. of tetrahydrofuran was treated portionwise with 110 g. of a commercial Raney nickel/water slurry over a 3 hr. period. The mixture was filtered through Celite and the filtrate was concentrated to a gummy residue. The residue was recrystallized from cyclohexane-benzene to yield 7.6 g. (43%) of product as tan needles, m.p. 167°-169° C.

Analysis: Calculated for $C_{14}H_{11}NO$: C, 80.36; H, 5.30; N, 6.69; Found: C, 80.47; H, 5.41; N, 6.67.

PREPARATION 5

3-Methylthio-4-phenylindolin-2-one m-Biphenylamine hydrochloride (35.3 g., 0.172 mole) was partitioned between 300 ml. of methylene chloride and 200 ml. of 5% sodium hydroxide solution. The layers were separated and the methylene chloride layer was dried (sodium sulfate) and its volume adjusted to 400 ml. with additional methylene chloride. The solution was cooled to −65° C. and 23.0 g. (0.172 mole) of ethyl 2-methylthioacetate was added. Immediately, 18.9 g. (0.175 mole) of t-butylhypochlorite was added dropwise. After addition was complete, the mixture was stirred at −65° C. for 1.5 hrs., treated with 17.2 g. (0.125 mole) of triethylamine and allowed to warm to ambient temperature. The methylene chloride solution was washed twice with two 100 ml. portions of water, concentrated, and the residue dissolved in 200 ml. of methanol. This solution was heated to reflux, treated with 40 ml. of 3 N hydrochloric acid and the mixture heated at reflux overnight. The dark solution was concentrated to approximately 100 ml. when a solid began to precipitate. The mixture was cooled, the solid was collected by filtration, washed with a small volume of cold methanol and dried to give 22.8 g. (52%) of yellow material. A nuclear magnetic resonance analysis of the material indicated that the solid was a mixture of the 4-phenyl isomer and the 6-phenyl isomer in a ratio of 2:1. The 4-phenyl isomer was separated from the 6-phenyl isomer by fractional crystallization from benzene. Three recrystallizations of the yellow solid from benzene gave 8.5 g. (19%) of 3-methylthio-4-phenylindolin-2-one as a white solid, m.p. 182°–5° C.

Analysis: Calculated for $C_{15}H_{13}NOS$: C, 70.56; H, 5.13; N, 5.49; Found: C, 70.26; H, 5.16; N, 5.14.

PREPARATION 6

4-Phenylindolin-2-one

A stirring solution of 3.5 g. (0.014 mole) of 4-phenyl-3-methylthioindolin-2-one in 75 ml. of tetrahydrofuran was treated portionwise with 20 g. of a commercial Raney nickel/water suspension. The mixture was filtered through Celite and the filtrate was concentrated to give a yellow solid. The solid was recrystallized to give a yellow solid. This solid was recrystallized from benzene to yield 1.6 g. (57%) of product as an off-white solid. An analytical sample was prepared from isopropanol; m.p. 192–194° C.

Analysis: Calculated for $C_{14}H_{11}NO$: C, 80.36; H, 5.30; N, 6.69; Found: C, 80.52; H, 5.41; N, 6.72.

PREPARATION 7

3-Methylthio-6-phenylindolin-2-one

The benzene mother liquors from Preparation 5 were concentrated at reduced pressure and the residue was dissolved in acetone. The solid which separated overnight was recrystallized twice from benzene to give 3.5 g. (8%) of 3-methylthio-6-phenylindolin-2-one as a tan solid, m.p. 177°–8° C. The structure was confirmed by the nuclear magnetic resonance spectrum.

Analysis: Calculated for $C_{15}H_{13}NOS$: C, 70.56; H, 5.13; N, 5.49; Found: C, 70.68; H, 5.13; N, 5.14.

PREPARATION 8

6-Phenylindolin-2-one

A mixture of 3.5 g. (0.014 mole) of 3-methylthio-6-phenylindolin-2-one, 7 g. of tin, 10 ml. of concentrated hydrochloric acid and 50 ml. of ethanol was refluxed 4 hours under nitrogen. The hot mixture was filtered and the filtrate concentrated to give a tan solid. The solid was further purified by vacuum sublimation at 0.01 mm. and 200° C. and then crystallized from benzene to give 0.5 g. (17%) of product as a white solid which melted at 173°–175° C.

Analysis: Calculated for $C_{14}H_{11}NO$: C, 80.36; H, 5.30; N, 6.69; Found: C, 80.74; H, 5.27; N, 6.75.

PREPARATION 9

When in the procedure of Preparation 1 and in the manner of the preceding discussion, 4-aminobiphenyl is replaced by equal molar amounts of the following:
  3-amino-5-methylbiphenyl,
  3-amino-4-methylbiphenyl,
  5-amino-2,2'-bitolyl,
  6-amino-2,2'-bitolyl,
  2-amino-5,4'-dimethylbiphenyl,
  4-amino-3,2'-dimethylbiphenyl,
  4-amino-2'-methylbiphenyl,
  2-amino-2',5'-dimethylbiphenyl,
  2-amino-4-methylbiphenyl,
  4-amino-3-methylbiphenyl,
  2-amino-6,2'-dimethylbiphenyl,
  2-amino-4,2'-dimethylbiphenyl,
  4-amino-3'-trifluoromethylbiphenyl,
  4-amino-4'-methoxybiphenyl,
  2-amino-4'-methoxybiphenyl,
  3-amino-2'-methoxybiphenyl,
  3-amino-2',5'-dimethoxybiphenyl,
  4-amino-4'-ethoxybiphenyl,
  2-amino-2'-methoxybiphenyl,
  4-amino-4'-fluorobiphenyl,
  3-amino-3'-chlorobiphenyl,
  2-amino-5-chlorobiphenyl,
  4-amino-4'-chlorobiphenyl,
  2-amino-5-bromobiphenyl,
  2-amino-4,5-dichlorobiphenyl,
  2-amino-4-chlorobiphenyl,
  2-amino-4'-chlorobiphenyl,
  2-amino-2'-chlorobiphenyl,
  2-amino-2'-bromobiphenyl,
  4-amino-3,2'-dibromobiphenyl,
  3-amino-3',5'-dibromobiphenyl,
  3-amino-4,2'-dichlorobiphenyl,
  2-amino-3',5'-dichlorobiphenyl,
  4-amino, 4'-tertiary butylbiphenyl (J. Chem. Soc. (C) 1966, pp 840–845),
  4-amino, 3-tertiary butylbiphenyl, there are obtained
  3-methylthio-6-methyl-4-phenylindolin-2-one and 3-methylthio-4-methyl-6-phenylindolin-2-one,
  3-methylthio-7-methyl-4-phenylindolin-2-one,
  3-methylthio-5-methyl-4-(2-methylphenyl)indolin-2-one and 3-methylthio-5-methyl-6-(2-methylphenyl)indolin-2-one,
  3-methylthio-6-methyl-7-(2-methylphenyl)indolin-2-one,
  3-methylthio-5-methyl-7-(4-methylphenyl)indolin-2-one,
  3-methylthio-7-methyl-5-(2-methylphenyl)indolin-2-one,
  3-methylthio-5-(2-methylphenyl)indolin-2-one,
  3-methylthio-7-(2,5-dimethylphenyl)indolin-2-one,
  3-methylthio-4-methyl-7-phenylindolin-2-one,
  3-methylthio-7-methyl-5-phenylindolin-2-one,
  3-methylthio-6-methyl-7-(2-methylphenyl)indolin-2-one,
  3-methylthio-4-methyl-7-(2-methylphenyl)indolin-2-one,
  3-methylthio-5-(3-trifluoromethylphenyl)indolin-2-one,
  3-methylthio-5-(4-methoxyphenyl)indolin-2-one,
  3-methylthio-7-(4-methoxyphenyl)indolin-2-one,
  3-methylthio-4-(2-methoxyphenyl)indolin-2-one and 3-methylthio-6-(2-methoxyphenyl)indolin-2-one,
  3-methylthio-4-(2,5-dimethoxyphenyl)indolin-2-one and 3-methylthio-6-(2,5-dimethoxyphenyl)indolin-2-one,
  3-methylthio-5-(4-ethoxyphenyl)indolin-2-one,
  3-methylthio-7-(2-methoxyphenyl)indolin-2-one,
  3-methylthio-5-(4-fluorophenyl)indolin-2-one,
  3-methylthio-4-(3-chlorophenyl)indolin-2-one and 3-methylthio-6-(3-chlorophenyl)indolin-2-one,
  3-methylthio-5-chloro-7-phenylindolin-2-one,
  3-methylthio-5-(4-chlorophenyl)indolin-2-one,
  3-methylthio-5-bromo-7-phenylindolin-2-one,
  3-methylthio-4,5-dichloro-7-phenyl-indolin-2-one,
  3-methylthio-4-chloro-7-phenylindolin-2-one,
  3-methylthio-4-chloro-7-(4-chlorophenyl)indolin-2-one,
  3-methylthio-7-(2-chlorophenyl)indolin-2-one,
  3-methylthio-7-(2-bromophenyl)indolin-2-one,
  3-methylthio-7-bromo-5-(2-bromophenyl)indolin-2-one, 3-methylthio-4-(3,5-dibromophenyl)indolin-2-one and 3-methylthio-6-(3,5-dibromophenyl)-indolin-2-one,
3-methylthio-7-chloro-4-(2-chlorophenyl)indolin-2-one,
3-methylthio-7-(3,5-dichlorophenyl)indolin-2-one;
3-methylthio-5-(4-tertiarybutylphenyl)indolin-2-one, and
3-methylthio-7-tertiarybutyl-5-phenylindolin-2-one.

PREPARATION 10

When in the procedure of Preparation 2 and in the manner of the preceding discussion, 3-methylthio-5-phenylindolin-2-one is replaced by equal molar amounts of the methylthioindolins prepared in Preparation 9, there are obtained
6-methyl-4-phenylindolin-2-one,
4-methyl-6-phenylindolin-2-one,
7-methyl-4-phenylindolin-2-one,
5-methyl-4-(2-methylphenyl)indolin-2-one,
5-methyl-6-(2-methylphenyl)indolin-2-one,
6-methyl-7-(2-methylphenyl)indolin-2-one,
5-methyl-7-(4-methylphenyl)indolin-2-one,
7-methyl-5-(2-methylphenyl)indolin-2-one,
5-(2-methylphenyl)indolin-2-one.
7-(2,5-dimethylphenyl)indolin-2-one,
4-methyl-7-phenylindolin-2-one,
7-methyl-5-phenylindolin-2-one,
6-methyl-7-(2-methylphenyl)indolin-2-one, 4-methyl-7-(2-methylphenyl)indolin-2-one,
5-(3-trifluoromethylphenyl)indolin-2-one,
5-(4-methoxyphenyl)indolin-2-one,
7-(4-methoxyphenyl)indolin-2-one,
4-(2-methoxyphenyl)indolin-2-one,
6-(2-methoxyphenyl)indolin-2-one,
4-(2,5-dimethoxyphenyl)indolin-2-one,
6-(2,5-dimethoxyphenyl)indolin-2-one,
5-(4-ethoxyphenyl)indolin-2-one,
7-(2-methoxyphenyl)indolin-2-one,
5-(4-fluorophenyl)indolin-2-one,
4-(3-chlorophenyl)indolin-2-one,
6-(3-chlorophenyl)indolin-2-one,
5-chloro-7-phenylindolin-2-one,
5-(4-chlorophenyl)indolin-2-one,
5-bromo-7-phenylindolin-2-one,
4,5-dichloro-7-phenylindolin-2-one,
4-chloro-7-phenylindolin-2-one,
4-chloro-7-(4-chlorophenyl)indolin-2-one,
7-(2-chlorophenyl)indolin-2-one,
7-(2-bromophenyl)indolin-2-one,
7-bromo-5-(2-bromophenyl)indolin-2-one,
4-(3,5-dibromophenyl)indolin-2-one,
6-(3,5-dibromophenyl)indolin-2-one,
7-chloro-4-(2-chlorophenyl)indolin-2-one,
7-(3,5-dichlorophenyl)indolin-2-one,
5-(4-tertiary butylphenyl)indolin-2-one,
7-tertiarybutyl-5-phenylindolin-2-one.

PREPARATION 11

When in the procedure of Preparation 1 and in the manner of the preceding discussion, 4-aminobiphenyl is replaced by equal molar amounts of the following nitro derivatives:
4-amino-4'-nitrobiphenyl,
2-amino-4'-nitrobiphenyl,
2-amino-2'-nitrobiphenyl,
4-amino-3-nitrobiphenyl,
4-amino-3'-nitrobiphenyl,
2-amino-5-nitrobiphenyl,
4-amino-2'-nitrobiphenyl,
3-amino-3'-nitrobiphenyl,
3-amino-2'-nitrobiphenyl
4-amino-2,2'-dimethyl-4-nitrobiphenyl,
2-amino-4,4'-dinitrobiphenyl,
4-amino-3,4'-dinitrobiphenyl,
3-amino-4,6-dinitrobiphenyl,
2-amino-5-chloro-4'-nitrobiphenyl,
4-amino-2-nitro-2'-chlorobiphenyl,
4-amino-3,3'-dimethyl-4'-nitrobiphenyl,
3-amino-4,4'-dinitrobiphenyl,
4-amino-2',4'-dinitrobiphenyl,
4-amino-2,2'-dinitrobiphenyl,
2-amino-2'-methyl-6'-nitrobiphenyl,
2-amino-5-bromo-4'-nitrobiphenyl,
4-amino-3-bromo-4'-nitrobiphenyl,
4-amino-3-nitro-2'-bromobiphenyl, there are obtained
3-methylthio-5-(4-nitrophenyl)indolin-2-one,
3-methylthio-7-(4-nitrophenyl)indolin-2-one,
3-methylthio-7-(2-nitrophenyl)indolin-2-one,
3-methylthio-5-phenyl-7-nitroindolin-2-one,
3-methylthio-5-(3-nitrophenyl)indolin-2-one,
3-methylthio-5-nitro-7-phenylindolin-2-one,
3-methylthio-5-(2-nitrophenyl)indolin-2-one,
3-methylthio-4-(3-nitrophenyl)indolin-2-one, and 3-methylthio-6-(3-nitrophenyl)indolin-2-one,
3-methylthio-4-(2-nitrophenyl)indolin-2-one, and 3-methylthio-6-(2-nitrophenyl)indolin-2-one,
3-methylthio-4-methyl-5-(2-methyl-4-nitrophenyl)indolin-2-one and 3-methylthio-6-methyl-5-(2-methyl-4-nitrophenyl)indolin-2-one,
3-methylthio-4-nitro-7-(4-nitrophenyl)indolin-2-one,
3-methylthio-5-(4-nitrophenyl)-7-nitroindolin-2-one,
3-methylthio-4-phenyl-5,7-dinitroindolin-2-one,
3-methylthio-5-chloro-7-(4-nitrophenyl)indolin-2-one,
3-methylthio-4-nitro-5-(2-chlorophenyl)indolin-2-one,
3-methylthio-5-(3-methyl-4-nitrophenyl)-7-methylindolin-2-one,
3-methylthio-4-nitro-7-(4-nitrophenyl)indolin-2-one,
3-methylthio-5-(2,4-dinitrophenyl)indolin-2-one,
3-methylthio-4-nitro-5-(2-nitrophenyl)indolin-2-one,
3-methylthio-7-(2-methyl-6-nitrophenyl)indolin-2-one,
3-methylthio-5-bromo-7-(4-nitrophenyl)indolin-2-one,
3-methylthio-5-(4-nitrophenyl)-7-bromoindolin-2-one,
3-methylthio-5-(2-bromophenyl)-7-nitroindolin-2-one.

PREPARATION 12

When in the procedure of Preparation 8 and in the manner of the preceding discussion, 3-methylthio-6-phenylindolin-2-one is replaced by equal molar amounts of the nitro-methylthioindolins of Preparation 11 and in addition sufficient extra molar amounts of tin (3 mols. tin extra per mole of nitro) and hydrochloric acid to reduce the nitro groups, there are obtained
5-(4-aminophenyl)indolin-2-one,
7-(4-aminophenyl)indolin-2-one,
7-(2-aminophenyl)indolin-2-one,
5-phenyl-7-aminoindolin-2-one,
5-(3-aminophenyl)indolin-2-one,
5-amino-7-phenylindolin-2-one,
5-(2-aminophenyl)indolin-2-one, 4-(3-aminophenyl)indolin-2-one and 6-(3-aminophenyl)indolin-2-one,
4-(2-aminophenyl)indolin-2-one and 6-(2-aminophenyl)indolin-2-one,
4-methyl-5-(2-methyl-4-aminophenyl)indolin-2-one,
6-methyl-5-(2-methyl-4-aminophenyl)indolin-2-one,
4-amino-7-(4-aminophenyl)indolin-2-one,
5-(4-aminophenyl)-7-aminoindolin-2-one,
4-phenyl-5,7-diaminoindolin-2-one,
5-chloro-7-(4-aminophenyl)indolin-2-one,
4-amino-5-(2-chlorophenyl)indolin-2-one,
5-(3-methyl-4-aminophenyl)-7-methylindolin-2-one,
4-amino-7-(4-aminophenyl)indolin-2-one,
5-(2,4-diaminophenyl)indolin-2-one,
4-amino-5-(2-aminophenyl)indolin-2-one,
7-(2-methyl-6-aminophenyl)indolin-2-one,
5-bromo-7-(4-aminophenyl)indolin-2-one,
5-(4-aminophenyl)-7-bromoindolin-2-one,
5-(2-bromophenyl)-7-aminoindolin-2-one.

EXAMPLE 1

2-Amino-3-biphenylacetic Acid Hydrate (1:4)

A mixture of 4.5 g. (0.0215 mole) of 7-phenylindolin-2-one and 60 ml. of 3 N sodium hydroxide was heated at reflux under nitrogen for 17 hrs. The reaction mixture was cooled, filtered, and the filtrate was diluted with 60 ml. of water. The solution was cooled, made acidic with glacial acetic acid and the resulting tan solid was immediately collected by filtration, washed with cold water and dried under vacuum to yield 4.6 g. (98%) of product as a tan solid, m.p. 98°–100° C. (dec.).

Analysis: Calculated for $C_{56}H_{54}N_4O_9$: C, 72.55; H, 5.87; N, 6.04; Found: C, 72.32; H, 5.67; N, 5.91.

EXAMPLE 2

2-Amino-6-biphenylacetic Acid

A mixture of 1.5 g. (0.007 mole) of 4-phenylindolin-2-one and 20 ml. of 3 N sodium hydroxide was refluxed for 6 hrs. The mixture was cooled and filtered. The filtrate was made acidic with glacial acetic acid, and the resulting solid was collected by filtration, washed with water and dried to yield 0.5 g. (32%) of product as a tan powder, m.p. 190°–191° C. (dec.).

Analysis: Calculated for $C_{14}H_{13}NO_2$: C, 73.99; H, 5.77; N, 6.16; Found: C, 73.54; H, 5.71; N, 6.28.

EXAMPLE 3

Sodium 2-amino-6-biphenylacetate

A solution of 2.8 g. (0.0125 mole) of crude 2-amino-6-biphenylacetic acid in 40 ml. of tetrahydrofuran was treated with 2 ml. of 5% sodium hydroxide. The solution was concentrated and the residue was subjected to a benzene azeotrope to eliminate water. The resulting tan solid was recrystallized three times from ethyl alcohol to give a pure sample of the sodium salt as a tan solid, m.p. 128°–48° C. (dec.).

Analysis: Calculated for $C_{14}H_{12}NaNO_2$: C, 67.46; H, 4.85; N, 5.62; Found: C, 67.25; H, 4.96; N, 5.65.

EXAMPLE 4

Sodium 2-amino-5-biphenylacetate Hydrate (3:4).

A mixture of 3.7 g. (0.0177 mole) of crude 5-phenylindolin-2-one and 50 ml. of 3 N sodium hydroxide was refluxed under a nitrogen atmosphere for 48 hrs. The reaction mixture was cooled and a solid immediately precipitated. The solid was collected by filtration, washed with a small volume of water, and recrystallized from 95% ethanol to give 1.9 g. (43%) of product as white plates, m.p. >285° C.

Analysis: Calculated for $C_{14}H_{12}NaNO_2.0.75\ H_2O$: C, 64.00; H, 5.18; N, 5.33; Found C, 64.09; H, 5.11; N, 5.46.

EXAMPLE 5

2-Amino-4-biphenylacetic Acid

When in the procedure of Example 2 and in the manner of the preceding discussion, 6-phenylindolin-2-one is replaced by an equal molar amount of 4-phenylindol-2-one, there is obtained 2-amino-4-biphenylacetic acid.

EXAMPLE 6

When in the procedure of Example 1 and in the manner of the preceding discussion, 7-phenylindolin-2-one is replaced by equal molar amounts of
6-methyl-4-phenylindolin-2-one,
4-methyl-6-phenylindolin-2-one,
7-methyl-4-phenylindolin-2-one,
5-methyl-4-(2-methylphenyl)indolin-2-one,
5-methyl-6-(2-methylphenyl)indolin-2-one,
6-methyl-7-(2-methylphenyl)indolin-2-one,
5-methyl-7-(4-methylphenyl)indolin-2-one,
7-methyl-5-(2-methylphenyl)indolin-2-one,
5-(2-methylphenyl)indolin-2-one,
7-(2,5-dimethylphenyl)indolin-2-one,
4-methyl-7-phenylindolin-2-one,
7-methyl-5-phenylindolin-2-one,
6-methyl-7-(2-methylphenyl)indolin-2-one,
4-methyl-7-(2-methylphenyl)indolin-2-one,
5-(3-trifluoromethylphenyl)indolin-2-one, there are obtained
2-amino-4-methyl-6-biphenylacetic acid,
2-amino-6-methyl-4-biphenylacetic acid,
2-amino-3-methyl-6-biphenylacetic acid,
2-amino-5,2'-dimethyl-6-biphenylacetic acid,
2-amino-5,2'-dimethyl-4-biphenylacetic acid,
2-amino-4,2'-dimethyl-3-biphenylacetic acid,
2-amino-5,4'-dimethyl-3-biphenylacetic acid,
2-amino-3,2'-dimethyl-5-biphenylacetic acid,
2-amino-2'-methyl-5-biphenylacetic acid,
2-amino-2',5'-dimethyl-3-biphenylacetic acid,
2-amino-6-methyl-3-biphenylacetic acid,
2-amino-3-methyl-5-biphenylacetic acid,
2-amino-4,2'-dimethyl-3-biphenylacetic acid,
2-amino-2',6-dimethyl-3-biphenylacetic acid,
2-amino-3'-trifluoromethyl-5-biphenylacetic acid.

EXAMPLE 7

When in the procedure of Example 1 and in the manner of the preceding discussion, 7-phenylindolin-2-one is replaced by equal molar amounts of
5-(4-methoxyphenyl)indolin-2-one,
7-(4-methoxyphenyl)indolin-2-one,
4-(2-methoxyphenyl)indolin-2-one,
6-(2-methoxyphenyl)indolin-2-one,
4-(2,5-dimethoxyphenyl)indolin-2-one,
6-(2,5-dimethoxyphenyl)indolin-2-one,
5-(4-ethoxyphenyl)indolin-2-one,
7-(2-methoxyphenyl)indolin-2-one, there are obtained
2-amino-4'-methoxy-5-biphenylacetic acid,
2-amino-4'-methoxy-3-biphenylacetic acid,
2-amino-2'-methoxy-6-biphenylacetic acid,
2-amino-2'-methoxy-4-biphenylacetic acid,
2-amino-2',5'-dimethoxy-6-biphenylacetic acid,
2-amino-2',5'-dimethoxy-4-biphenylacetic acid,
2-amino-4'-ethoxy-5-biphenylacetic acid, 2-amino-4'-methoxy-3-biphenylacetic acid.

EXAMPLE 8

When in the manner of Example 1 and in the manner of the preceding discussion, 7-phenylindolin-2-one is replaced by equal molar amounts of
5-(4-fluorophenyl)indolin-2-one,
4-(3-chlorophenyl)indolin-2-one,
6-(3-chlorophenyl)indolin-2-one,
5-chloro-7-phenylindolin-2-one,
5-(4-chlorophenyl)indolin-2-one,
5-bromo-7-phenylindolin-2-one,
4,5-dichloro-7-phenylindolin-2-one,
4-chloro-7-phenylindolin-2-one,
4-chloro-7-(4-chlorophenyl)indolin-2-one,
7-(2-chlorophenyl)indolin-2-one, 7-(2-bromophenyl)indolin-2-one,
7-bromo-5-(2-bromophenyl)indolin-2-one,
4-(3,5-dibromophenyl)indolin-2-one,
6-(3,5-dibromophenyl)indolin-2-one,
7-chloro-4-(2-chlorophenyl)indolin-2-one,
7-(3,5-dichlorophenyl)indolin-2-one,
5-(tertiarybutylphenyl)indolin-2-one,
7-tertiarybutyl-5-phenylindolin-2-one, there are obtained.
2-amino-4'-fluoro-5-biphenylacetic acid,
2-amino-3'-chloro-6-biphenylacetic acid,
2-amino-3'-chloro-4-biphenylacetic acid,
2-amino-5-chloro-3-biphenylacetic acid,
2-amino-4'-chloro-5-biphenylacetic acid,
2-amino-5-bromo-3-biphenylacetic acid,
2-amino-5,6-dichloro-3-biphenylacetic acid,
2-amino-6-chloro-3-biphenylacetic acid,
2-amino-4',6-dichloro-3-biphenylacetic acid,
2-amino-2'-chloro-3-biphenylacetic acid,
2-amino-2'-bromo-3-biphenylacetic acid,
2-amino-3,2'-dibromo-5-biphenylacetic acid,
2-amino-3',5'-dibromo-6-biphenylacetic acid,
2-amino-2'-3-dichloro-6-biphenylacetic acid,
2-amino-3',5'-dichloro-3-biphenylacetic acid,
2-amino-4'-tertiarybutyl-5-biphenylacetic acid,
2-amino-3-tertiarybutyl-5-biphenylacetic acid.

EXAMPLE 9

When in the procedure of Example 1, 2 moles of potassium hydroxide per mol of the indolin-2-one is substituted for the sodium hydroxide, ethanol is substituted for water and 7-phenylindolin-2-one is replaced by equal molar amounts of
5-(4-aminophenyl)indolin-2-one,
7-(4-aminophenyl)indolin-2-one,
7-(2-aminophenyl)indolin-2-one,
5-phenyl-7-aminoindolin-2-one,
5-(3-aminophenyl)indolin-2-one,
5-amino-7-phenylindolin-2-one,
5-(2-aminophenyl)indolin-2-one,
4-(3-aminophenyl)indolin-2-one,
6-(3-aminophenyl)indolin-2-one,
4-(2-aminophenyl)indolin-2-one,
6-(2-aminophenyl)indolin-2-one,
4-methyl-5-(2-methyl-4-aminophenyl)indolin-2-one,
6-methyl-5-(2-methyl-4-aminophenyl)indolin-2-one,
4-amino-7-(4-aminophenyl)indolin-2-one, there are obtained
2,4'-diamino-5-biphenylacetic acid,
2,4'-diamino-3-biphenylacetic acid,
2,2'-diamino-3-biphenylacetic acid,
2,3-diamino-5-biphenylacetic acid,
2,3'-diamino-5-biphenylacetic acid,
2,5-diamino-3-biphenylacetic acid,
2,2'-diamino-5-biphenylacetic acid,
2,3'-diamino-6-biphenylacetic acid,
2,3'-diamino-4-biphenylacetic acid,
2,2'-diamino-6-biphenylacetic acid,
2,2'-diamino-4-biphenylacetic acid,
2,4'-diamino-2',6-dimethyl-5-biphenylacetic acid,
2,4'-diamino-2',4-dimethyl-5-biphenylacetic acid,
2,4',6-triamino-3-biphenylacetic acid.

EXAMPLE 10

When in the procedure of Example 1, two moles of potassium hydroxide per mol of the phenylindolin-2-one is substituted for the sodium hydroxide, ethanol is substituted for water and 7-phenylindolin-2-one is replaced by equal molar amounts of
5-(4-aminophenyl)-7-aminoindolin-2-one,
4-phenyl-5,7-diaminoindolin-2-one,
5-chloro-7-(4-aminophenyl)indolin-2-one,
4-amino-5-(2-chlorophenyl)indolin-2-one,
5-(3-methyl-4-aminophenyl)-7-methylindolin-2-one,
4-amino-7-(4-aminophenyl)indolin-2-one,
5-(2,4-diaminophenyl)indolin-2-one,
4-amino-5-(2-aminophenyl)indolin-2-one,
7-(2-methyl-6-aminophenyl)indolin-2-one,
5-bromo-7-(4-aminophenyl)indolin-2-one,
5-(4-aminophenyl-7-bromoindolin-2-one,
5-(2-bromophenyl)-7-aminoindolin-2-one, there are obtained
2,3,4'-triamino-5-biphenylacetic acid,
2,3,5-triamino-6-biphenylacetic acid,
2,4'-diamino-5-chloro-3-biphenylacetic acid,
2,6-diamino-2'-chloro-3-biphenylacetic acid,
2,4'-diamino-3,3'-dimethyl-5-biphenylacetic acid,
2,6,4'-triamino-3-biphenylacetic acid,
2,2',4'-triamino-5-biphenylacetic acid,
2,2',6-triamino-3-biphenylacetic acid,
2,2'-amino-6'-methyl-3-biphenylacetic acid,
2,4'-diamino-5-bromo-3-biphenylacetic acid,
2,4'-diamino-3-bromo-3-biphenylacetic acid,
2,3-diamino-2'-bromo-5-biphenylacetic acid.

EXAMPLE 11

Ethyl-2-amino-4-biphenylacetate

Sodium 2-amino-4-biphenylacetate is dissolved in dimethylformamide and the solution treated with ethyliodide. The solution is stirred at room temperature for about 3 hours, the solution added to water and the mixture extracted several times with benzene. The combined benzene extracts are washed with dilute base and water, dried over sodium sulfate, concentrated and crystallized to give ethyl-2-amino-4-biphenylacetate.

FORMULATION AND ADMINISTRATION

The present invention also contemplates novel compositions containing the compounds of the present invention as active ingredients. Effective quantities of any of the foregoing pharmacologically active compounds may be administered to a living animal body in any one of various ways. For example, they may be orally administered in the form of sterile solutions. In forming the novel compositions of this invention, the active ingredient is incorporated in a suitable carrier such as a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmaceutically active compounds of the present invention may be advantageously employed in a unit dosage of from about 1 to about 50 milligrams. The unit dosage may be given a suitable number of times daily so that the daily dosage may vary from 1 to 450 milligrams. Five to 25 milligrams appears to be an optimum unit dose.

It is only necessary that the active ingredients constitute an effective amount, i.e., such that a suitable effective dosage will be obtained consistent with the dosage employed. The exact individual dosages as well as daily dosages will, of course, be determined according to standard medical principles under the direction of a physician or veterinarian.

The active agents of the present invention may be combined with other pharmacologically active agents, or with buffers, antacids or the like, for administration. The proportion of the active agent in the compositions may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | | Per capsule mg. |
|---|---|---|
| Active ingredient | | 5.0 |
| Lactose | | 296.7 |
| Starch | | 129.0 |
| Magnesium stearate | | 4.3 |
| | Total | 435.0 mg. |

Additional capsule formulations preferably contain a higher dosage of active ingredient and are as follows:

| Ingredients | | Per capsule mg. |
|---|---|---|
| Active ingredient | | 25.0 |
| Lactose | | 306.5 |
| Starch | | 99.2 |
| Magnesium stearate | | 4.3 |
| | Total | 435.0 mg. |

In each case, the selected active ingredient is uniformly blended with lactose, starch, and magnesium stearate and the blend encapsulated.

2. Tablets

A typical formulation for a tablet containing 5.0 mg. of active ingredient per tablet is as follows. The formulation may be used for other strengths of active ingredient by adjusting the weight of the dicalcium phosphate.

| | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| | 170.1 mg. |

The tablets are formed by uniformly blending ingredients 1, 2, 4 and 5. Ingredient 3 is prepared as a 10 percent paste in water. The blend is granulated with starch paste and the resulting wet mass passed through an eight mesh screen. The wet granulation is dried and sized through a twelve mesh screen. The dried granules are blended with the calcium stearate and pressed.

3. Injectable—2% sterile solutions

| | Per cc. |
|---|---|
| Active ingredient | 20 mg. |
| Preservative, e.g., chlorobutanol | 0.5% weight/volume |
| Water for injection | q.s. |

The solution is prepared, classified by filtration, and placed into vials. The vials are sealed and heated in an autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

I claim:

1. A method for alleviating inflammation in a living animal body with a minimum of undesirable side effects comprising internally administering to said living animal body an effective amount of a compound having the formula:

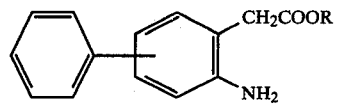

wherein R is hydrogen lower alkyl, sodium or potassium, and the phenyl substituent is in the 3, 4, or 5 position and hydrates thereof.

2. The method of claim 1 wherein the compound is 2-amino-4-biphenylacetic acid.

3. The method of claim 1 wherein the compound is 2-amino-5-biphenylacetic acid.

4. The method of claim 1 wherein the compound is 2-amino-3-biphenylacetic acid.

5. The method of claim 1 wherein the compound is in the form of a hydrate.

6. The method of claim 1 wherein the compound is sodium 2-amino-4-biphenylacetate.

7. The method of claim 1 wherein the compound is sodium 2-amino-3-biphenylacetic acid hydrate (1:4).

8. The method of claim 1 wherein the compound is sodium 2-amino-5-biphenylacetate hydrate (3:4).

* * * * *